United States Patent
Kapsner et al.

(10) Patent No.: US 9,242,930 B2
(45) Date of Patent: Jan. 26, 2016

(54) MILD ANIONIC SURFACTANTS SUITABLE FOR PERSONAL CARE COMPOSITIONS

(75) Inventors: Timothy Roland Kapsner, Minnepolis, MN (US); Daniel Thomas Nowlan, III, Hugo, MN (US)

(73) Assignee: ELC Management LLC, New York, NY (US)

( * ) Notice: Subject to any disclaimer, the term of this patent is extended or adjusted under 35 U.S.C. 154(b) by 463 days.

(21) Appl. No.: 13/444,590

(22) Filed: Apr. 11, 2012

(65) Prior Publication Data

US 2013/0102803 A1    Apr. 25, 2013

Related U.S. Application Data

(60) Provisional application No. 61/475,141, filed on Apr. 13, 2011.

(51) Int. Cl.
| | | |
|---|---|---|
| C07C 309/12 | (2006.01) | |
| C11D 1/04 | (2006.01) | |
| C11D 1/10 | (2006.01) | |
| C11D 1/12 | (2006.01) | |
| C11D 1/28 | (2006.01) | |
| C11D 1/66 | (2006.01) | |
| A61K 8/46 | (2006.01) | |
| A61Q 5/02 | (2006.01) | |
| C07C 305/10 | (2006.01) | |
| C07C 309/17 | (2006.01) | |

(52) U.S. Cl.
CPC .............. *C07C 309/12* (2013.01); *A61K 8/463* (2013.01); *A61K 8/466* (2013.01); *A61Q 5/02* (2013.01); *C07C 305/10* (2013.01); *C07C 309/17* (2013.01); *C11D 1/04* (2013.01); *C11D 1/10* (2013.01); *C11D 1/123* (2013.01); *C11D 1/28* (2013.01); *C11D 1/667* (2013.01)

(58) Field of Classification Search
None
See application file for complete search history.

(56) References Cited

U.S. PATENT DOCUMENTS

| | | | |
|---|---|---|---|
| 3,544,613 A | 12/1970 | Knaggs et al. | |
| 3,869,412 A * | 3/1975 | Waag | 510/467 |
| 4,301,044 A * | 11/1981 | Wentler et al. | 510/494 |
| 4,363,763 A * | 12/1982 | Peterson | 536/119 |
| 4,515,929 A | 5/1985 | Tang | |
| 4,611,008 A | 9/1986 | Heinzelmann | |
| 4,664,835 A | 5/1987 | Grollier et al. | |
| 4,973,686 A | 11/1990 | Kretschmann et al. | |
| 5,310,508 A | 5/1994 | Subramanyam et al. | |
| 5,366,665 A | 11/1994 | Cho | |
| 5,633,362 A | 5/1997 | Nagarajan et al. | |
| 5,646,100 A | 7/1997 | Haugk et al. | |
| 5,686,276 A | 11/1997 | Laffend et al. | |
| 5,716,604 A | 2/1998 | Coe et al. | |
| 5,821,092 A | 10/1998 | Nagarajan et al. | |
| 5,834,517 A | 11/1998 | O'Lenick, Jr. | |
| 6,025,184 A | 2/2000 | Laffend et al. | |
| 6,136,576 A | 10/2000 | Diaz-Torres et al. | |
| 6,271,246 B1 | 8/2001 | Murad | |
| 6,361,983 B1 | 3/2002 | Ames | |
| 6,406,895 B1 | 6/2002 | Defretin et al. | |
| 6,428,767 B1 | 8/2002 | Burch et al. | |
| 6,479,716 B2 | 11/2002 | Hilaly et al. | |
| 6,555,700 B1 | 4/2003 | Horrobin et al. | |
| 7,098,368 B2 | 8/2006 | Seapan et al. | |
| 7,759,393 B2 | 7/2010 | Joerger et al. | |
| 8,048,920 B2 | 11/2011 | Joerger et al. | |
| 2003/0082756 A1 | 5/2003 | Burch et al. | |
| 2004/0110655 A1 | 6/2004 | Yamashita et al. | |
| 2005/0069997 A1 | 3/2005 | Adkesson et al. | |
| 2005/0192187 A1 | 9/2005 | Wagner et al. | |

(Continued)

FOREIGN PATENT DOCUMENTS

| | | |
|---|---|---|
| CN | 101426923 | 5/2009 |
| CN | 101641313 | 2/2010 |

(Continued)

OTHER PUBLICATIONS

WO 99/09935A2, Hensen, et al., Cosmetic Preparations, 1999, English translation, 15 pages.*
WO 99/09938A1, Hensen, et al., Cosmetic agents containing faty acid polyglyceol ester sulphates, 1999, English translation, 13 pages.*
PCT International Search Report; International Application No. PCT/US2012/033134; Completion Date: Oct. 26, 2012; Date of Mailing: Oct. 29, 2012.
PCT International Search Report; International Application No. PCT/US2012/033136; Completion Date: Oct. 26, 2012; Date of Mailing: Oct. 29, 2012.
PCT Written Opinion of the tnternalional Searching Authority; International Application No. PCT/US2012/033134; Completion Date: Oct. 26, 2012; Mailing Date: Oct. 29, 2012.

(Continued)

*Primary Examiner* — Yate K Cutliff
(74) *Attorney, Agent, or Firm* — Idris McKelvey

(57) ABSTRACT

A surfactant represented by the formula:

$$R_1 \overset{O}{\underset{}{\|}}\!\!-\!\!O\!\!-\!\!(CH_2)_m\!\!-\!\!\overset{R_2}{\underset{}{C}H}\!\!-\!\!OR_3$$

wherein:
$R_1$ is $CH_3(CH_2)_m$ and may be interrupted with at least one heteroatom selected from the group consisting of amine, ether, ester, amide, sulfur, sulfur monoxide, sulfer dioxide, sulfamate, hydroxy, or mixtures thereof; and
$m=6-16$
$n=0$ or $1$
$R_2=H$ or $CH_3$; and
$R_3=H$, $SO_3X$, $CO(CH)_2COOH$, or $COCH(SO_3X)CH_2COOX_1$;
wherein X and $X_1$ are the same or different, and each is selected from $NH_4^+$, an alkali metal, or an H atom.

7 Claims, No Drawings

(56) References Cited

U.S. PATENT DOCUMENTS

| | | |
|---|---|---|
| 2006/0148053 A1 | 7/2006 | Emptage et al. |
| 2007/0207113 A1 | 9/2007 | Joerger et al. |
| 2007/0207939 A1 | 9/2007 | Fenyvesl et al. |
| 2008/0051592 A1 | 2/2008 | McNeff et al. |
| 2008/0319236 A1 | 12/2008 | McNeff et al. |
| 2009/0155383 A1 | 6/2009 | Kitko et al. |
| 2010/0034761 A1 | 2/2010 | Fenyvesi et al. |
| 2011/0306665 A1 | 12/2011 | Kobayashi et al. |
| 2013/0101541 A1 * | 4/2013 | Kapsner et al. .............. 424/70.1 |

FOREIGN PATENT DOCUMENTS

| | | | |
|---|---|---|---|
| EP | 2 272 492 | | 1/2011 |
| GB | 1419351 | | 12/1975 |
| JP | S5051506 | * | 5/1975 |
| JP | 06-287114 | | 10/1994 |
| WO | WO-93/25646 | | 12/1993 |
| WO | WO 93/25646 | * | 12/1993 ............... C11D 1/28 |
| WO | WO 99/09935 A2 | * | 3/1999 ............... A61K 7/00 |
| WO | WO 99/09938 A1 | * | 3/1999 ............... A61K 7/06 |
| WO | WO-2007095255 | | 8/2007 |
| WO | WO 2010/100887 | | 9/2010 |
| WO | WO-2011/109047 | | 9/2011 |

OTHER PUBLICATIONS

PCT Written Opinion of the International Searching Authority; International Application No. PCT/US2012/033136; Completion Date: Oct. 26, 2012; Mailing Date: Oct. 29, 2012.

Supplemental European Search Report: EP12771817.9; Mailing Date: Nov. 12, 2014; Coimpletion Date: Nov. 3, 2014.

Supplemental European Search Report; EP12771291; Completion Date: Nov. 26, 2014; Mailing Date: Dec. 8, 2014.

* cited by examiner

MILD ANIONIC SURFACTANTS SUITABLE FOR PERSONAL CARE COMPOSITIONS

CROSS-REFERENCE TO RELATED APPLICATIONS

The present application claims priority from U.S. Provisional Application No. 61/475,141, filed Apr. 13, 2011.

TECHNICAL FIELD

This invention relates to new mild anionic surfactants. In particular, the invention relates to a novel sulfate ester surfactant and sulfosuccinate surfactant which may be derived from natural feedstocks.

BACKGROUND OF THE INVENTION

Surfactants are well known materials which are used broadly for industrial and personal uses. For example, surfactants are often used as rheology modifiers for drilling applications. And in other instances, surfactants are used in detergent compositions, such as hard surface cleaners, laundry detergents, and personal care compositions.

The demand for mild surfactant compounds in the area of detergents, personal products, cosmetics, oral hygiene and pharmaceuticals has been steadily rising. Recent advances in esterification and transesterification techniques have surprisingly enabled development of novel surfactants which may be sourced from a wide variety of feedstocks.

In general, most compositions contain surfactants derived from petrochemicals. Since petro-chemicals can sometimes have handling, storage, and environmental hazards associated with them, it would be most desirable to use surfactants which are instead derived from agriculturally grown materials, such as vegetable oil fatty acids. These naturally occurring compounds have the distinct advantage of being readily available, inexpensive, biodegradable, and aquatically favorable.

One of the drawbacks of naturally derived anionic surfactants has been an apparent decline in cleaning performance versus more traditional petrochemical surfactants. Among surfactants generally formed from petrochemical sources, sodium lauryl sulfate (SLS) is considered to be a highly effective surfactant for removing oil and residues. Shampoo compositions, for example, typically combine sodium lauryl sulfate and/or sodium laureth sulfate, and another co-surfactant. SLS is generally combined with other surfactants, and used in relatively low concentrations, because it is known to irritate sensitive skin. Baby shampoos may exclude SLS altogether because it may cause skin and eye irritation in small children. Therefore, there is a need for a mild surfactant which may supplement SLS in personal care compositions.

Based on the foregoing, there is a need for mild anionic surfactants which may be derived from petrochemical sources, but which may also be derived from natural and sustainable feedstocks, and which has excellent cleansing, foaming, viscosity building, and dermatological compatibility.

SUMMARY OF THE INVENTION

A surfactant represented by the formula:

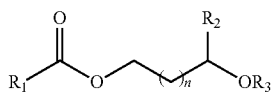

wherein:

$R_1$ is $CH_3(CH_2)_m$ and may be interrupted with at least one heteroatom selected from the group consisting of amine, ether, ester, amide, sulfur, sulfur monoxide, sulfer dioxide, sulfamate, hydroxy, or mixtures thereof; and m=6-16 n=0 or 1

$R_2$=H or $CH_3$; and $R_3$=H, $SO_3X$, $CO(CH)_2COOH$, or $COCH(SO_3X)CH_2COOX_1$;

wherein X and $X_1$ are the same or different, and each is selected from $NH_4^+$, an alkali metal, an H atom.

The invention further relates to methods of making the surfactant herein, as well as to compositions comprising the surfactant and uses thereof.

DETAILED DESCRIPTION

While the specification concludes with claims that particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level, and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain.

The term "personal care composition" as used herein, unless otherwise specified, refers to the compositions of the present invention, wherein the compositions are intended to include only those compositions for topical application to the hair or skin, and specifically excludes those compositions that are directed primarily to other applications such as hard surface cleansing, fabric or laundry cleansing, and similar other applications not intended primarily for topical application to the hair or skin.

The term "polymer" as used herein shall include materials whether made by polymerization of one type of monomer or made by two (i.e., copolymers) or more types of monomers.

The term "solid particle" as used herein means a particle that is not a liquid or a gas.

The term "water-soluble" as used herein, means that the polymer is soluble in water in the present composition. In general, the polymer should be soluble at 25° C. at a concentration of at least 0.1% by weight of the water solvent, preferably at least 1%, more preferably at least 5%, most preferably at least 15%.

The term "water-insoluble" as used herein, means that a compound is not soluble in water in the present composition. Thus, the compound is not miscible with water.

Surfactant

The surfactants herein conform to the general formula I:

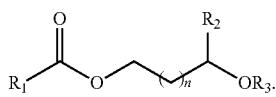

wherein:

$R_1$ is $CH_3(CH_2)_m$ and may be interrupted with at least one heteroatom selected from the group consisting of amine, ether, ester, amide, sulfur, sulfur monoxide, sulfer dioxide, sulfamate, hydroxy, or mixtures thereof; and m=6-16 n=0 or 1

$R_2$=H or $CH_3$; and $R_3$=H, $SO_3X$, $CO(CH)_2COOH$, or $COCH(SO_3X)CH_2COOX_1$; and wherein X and $X_1$ are the same or different, and each is selected from $NH_4^+$, an alkali metal, an H atom. Preferably, the alkali metals are selected from sodium ($Na^+$) or potassium ($K^+$).

In one embodiment, $R_1$ may be branched, alkyl, or alkenyl. If $R_1$ is alkenyl, it preferably comprises no more than one double bond. While "m" may be $C_6$ to $C_{16}$, it is more preferably $C_8$ to $C_{14}$, and most preferably from $C_{10}$ to $C_{12}$.

In one embodiment, the surfactant has a structure according to formula II:

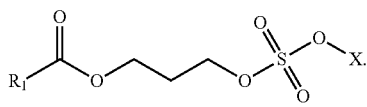

wherein $R_1$ is $C_8$-$C_{18}$ alkyl; and
X is selected from $NH_4^+$, an alkali metal, or an H atom.

In a preferred embodiment, the surfactant is a sodium lauryl propanediol ester sulfate having the formula:

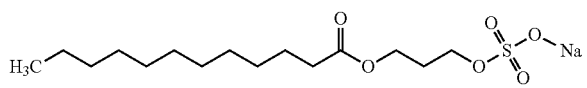

In yet another embodiment, the surfactant has a structure according to formula III:

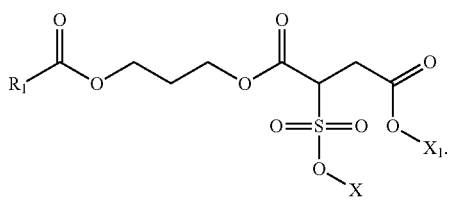

wherein $R_1$ is $C_8$-$C_{18}$ alkyl; and
X and $X_1$ are the same or different, and each is selected from $NH_4^+$, an alkali metal, or an H atom.

In a preferred embodiment, the surfactant is a disodium propanediol lauryl sulfosuccinate according to the formula:

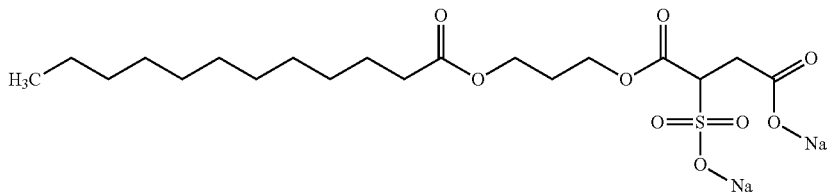

Esterfication techniques suitable for forming precursors to the surfactants herein are described in U.S. Patent Publication Numbers 2008/0051592 and 2008/0319236. Further surfactant synthesis and sulfation techniques are described in U.S. Pat. Nos. 5,834,517, 3,544,613, and 4,973,686.

While the surfactants herein may be derived from traditional petrochemical sources, in one embodiment, the surfactants are preferably derived from natural sources and considered "green" and environmentally friendly. For the purpose of this invention the term "naturally derived" means that the surfactants herein are not formed from petrochemical feedstocks. Petroleum oils are, of course, naturally occurring materials. But the term "natural" is used herein to exclude materials which have been formed from synthetic or petrochemical chemicals. While the surfactants herein may be combined with other synthetic or petrochemical-based ingredients and co-surfactants, in one embodiment, the surfactants per-se may be considered to be naturally derived.

The surfactants herein are suitable for various home and personal care compositions. For example, the surfactants may be present in laundry detergents, dish washing detergents, hard surface cleaners, body washes, shampoos, facial cleansers, and other compositions used in the home or on the body. Since the compositions are believed to be particularly mild to the skin, body washes and shampoos are particularly well suited for such surfactants. When formulated in a personal care composition, the surfactants may be present at a level of from about 0.5% to about 25%, preferably from about 0.8% to about 20%, and most preferably from about 1% to about 15%.

In one embodiment, the surfactants may be present in a single phase or in a visually distinct multi-phase personal care composition. At least one of the visually distinct phases may comprise a cleansing phase which includes a surfactant component. The surfactant component may comprise one or more surfactants, and the multiple phases may be in physical contact with one another. Such multi-phase compositions are described in U.S. Patent Application Number 2005/0192187.

Cosmetically Acceptable Medium

Embodiments including the surfactant as a component of a personal care composition comprise a cosmetically acceptable medium. The level and species of the medium are selected according to the compatibility with other components and other desired characteristic of the product. Generally, the cosmetically acceptable medium is present in an amount from about 20% to about 95% by weight of the composition. A cosmetically acceptable medium may be selected such that the composition of the present invention may be in the form of, for example, a pourable liquid, a gel, a paste, a dried powder, or a dried film.

Cosmetically acceptable mediums useful in the present invention include water and water solutions of lower alkyl alcohols. Lower alkyl alcohols useful herein are monohydric alcohols having 1 to 6 carbons, and preferably are selected from ethanol and isopropanol.

In cosmetic applications, the pH of the present composition, measured neat, is preferably from about 3 to about 9, more preferably from about 4 to about 8.

In automatic dishwashing compositions, the pH may be from about 7 to about 13, more preferably from about 8 to about 12, and most preferably from about 9 to about 10.

Buffers and other pH-adjusting agents can be included to achieve the desirable pH.

Oily Conditioning Agent

In a preferred embodiment of the present invention, the personal care compositions comprise one or more oily conditioning agents. Oily conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the compositions of the present invention typically comprise a water-insoluble, water-dispersible, non-volatile, liquid that forms emulsified, liquid particles. Suitable oily conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

One or more oily conditioning agents are typically present at a concentration from about 0.01% to about 10%, preferably from about 0.1% to about 8%, more preferably from about 0.2% to about 4%, by weight of the composition.

Silicone Conditioning Agent

The invention herein may include one or more oily conditioning agents. Such oily conditioning agents may include a water-soluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 5,000 to about 1,500,000 csk, more preferably from about 10,000 to about 1,000,000 csk.

In an embodiment including a generally opaque composition, the personal care composition comprises a non-volatile silicone oil having a particle size as measured in the personal care composition from about 1 µm to about 50 µm. In an embodiment which may be transparent, translucent, or opaque, the personal care composition comprises a non-volatile silicone oil having a particle size as measured in the personal care composition from about 100 nm to about 1 µm. One embodiment comprises a non-volatile silicone oil having a particle size as measured in the personal care composition of less than about 100 nm.

Non-volatile silicone oils suitable for use in the compositions may be selected from organo-modified silicones and fluoro-modified silicones. In one embodiment of the present invention, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

In a preferred embodiment of the present invention, the non-volatile silicone oil is dimethicone.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

Organic Conditioning Oils

The oily conditioning agent may also comprise at least one organic conditioning oil, either alone or in combination with other conditioning agents, such as the silicones described above.

Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include 2,2,4,4,6,6,8,8-dimethyl-10-methylundecane and 2,2,4,4,6,6-dimethyl-8-methylnonane, available from Permethyl Corporation. A preferred hydrocarbon polymer is polybutene, such as the copolymer of isobutylene and butene, which is commercially available as L-14 polybutene from Amoco Chemical Corporation.

Polyolefins

Organic conditioning oils can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

Fatty Esters

Other suitable organic conditioning oils include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are those known as polyhydric alcohol esters. Such polyhydric alcohol esters include alkylene glycol esters.

Still other fatty esters suitable for use in the compositions of the present invention are glycerides, including, but not limited to, mono-, di-, and tri-glycerides, preferably di- and tri-glycerides, more preferably triglycerides. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones. Specific non-limiting examples of suitable fluorinated compounds include the Fomblin product line from Ausimont which includes HC/04, HC/25, HC01, HC/02, HC/03; Dioctyldodecyl Fluoroeptyl Citrate, commonly called Biosil Basics Fluoro Gerbet 3.5 supplied by Biosil Technologies; and Biosil Basics Fluorosil LF also supplied by Biosil Technologies.

Fatty Alcohols

Other suitable organic conditioning oils for use in the personal care compositions of the present invention include, but are not limited to, fatty alcohols having at least about 10 carbon atoms, more preferably about 10 to about 22 carbon atoms, most preferably about 12 to about 16 carbon atoms. Also suitable for use in the personal care compositions of the present inventions are alkoxylated fatty alcohols which conform to the general formula:

$$CH_3(CH_2)_nCH_2(OCH_2CH_2)_pOH$$

wherein n is a positive integer having a value from about 8 to about 20, preferably about 10 to about 14, and p is a positive integer having a value from about 1 to about 30, preferably from about 2 to about 23.

Alkyl Glucosides and Alkyl Glucoside Derivatives

Suitable organic conditioning oils include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

Other Conditioning Agents

Quaternary Ammonium Compounds

Suitable quaternary ammonium compounds include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

Examples of other useful quaternary ammonium surfactants include, but are not limited to, Quaternium-33, Quaternium-43, isostearamidopropyl ethyldimonium ethosulfate, Quaternium-22 and Quaternium-26, or combinations thereof, as designated in the CTFA Dictionary.

Other hydrophilic quaternary ammonium compounds useful in a composition of the present invention include, but are not limited to, Quaternium-16, Quaternium-27, Quaternium-30, Quaternium-52, Quaternium-53, Quaternium-56, Quaternium-60, Quaternium-61, Quaternium-62, Quaternium-63, Quaternium-71, and combinations thereof.

Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

Additional Components

The personal care compositions may further comprise one or more additional components known for use in hair care or personal care products, provided that the additional components are physically and chemically compatible with the essential components described herein, or do not otherwise unduly impair product stability, aesthetics or performance. Individual concentrations of such additional components may range from about 0.001% to about 10% by weight of the personal care compositions.

Non-limiting examples of additional components for use in the composition include natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculicides, pH adjusting agents, perfumes, preservatives, chelants, proteins, skin active agents, sunscreens, UV absorbers, and vitamins.

Cellulose or Guar Cationic Deposition Polymers

The personal care compositions of the present invention may also include cellulose or guar cationic deposition polymers. Generally, such cellulose or guar cationic deposition polymers may be present at a concentration from about 0.05% to about 5%, by weight of the composition. Suitable cellulose or guar cationic deposition polymers have a molecular weight of greater than about 5,000. Additionally, such cellulose or guar deposition polymers have a charge density from about 0.5 meq/g to about 4.0 meq/g at the pH of intended use of the personal care composition. The pH of the compositions of the present invention are measured neat.

Suitable cellulose or guar cationic polymers include those which conform to the following formula:

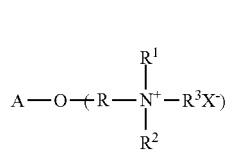

wherein A is an anhydroglucose residual group, such as a cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, the cellulose or guar cationic polymers are salts of hydroxyethyl cellulose reacted with trimethyl ammonium substituted epoxide, referred to in the industry (CTFA) as Polyquaternium 10 and available from Amerchol Corp. (Edison, N.J., USA).

Synthetic Cationic Deposition Polymers

The personal care compositions of the present invention may also include synthetic cationic deposition polymers. Generally, such synthetic cationic deposition polymers may be present at a concentration from about 0.025% to about 5%, by weight of the composition. Such synthetic cationic deposition polymers have a molecular weight from about 1,000 to about 5,000,000. Additionally, such synthetic cationic deposition polymers have a charge density from about 0.5 meq/g to about 10 meq/g.

Suitable synthetic cationic deposition polymers include those which are water-soluble or dispersible, cationic, non-crosslinked, conditioning copolymers comprising: (i) one or more cationic monomer units; and (ii) one or more nonionic monomer units or monomer units bearing a terminal negative charge; wherein said copolymer has a net positive charge, a cationic charge density of from about 0.5 meq/g to about 10 meq/g, and an average molecular weight from about 1,000 to about 5,000,000.

Non-limiting examples of suitable synthetic cationic deposition polymers are described in United States Patent Application Publication US 2003/0223951 A1 to Geary et al.

Anti-Dandruff Actives

The compositions may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

Azole anti-microbials include imidazoles such as climbazole and ketoconazole.

Selenium sulfide compounds are described, for example, in U.S. Pat. No. 2,694,668; U.S. Pat. No. 3,152,046; U.S. Pat. No. 4,089,945; and U.S. Pat. No. 4,885,107.

Sulfur may also be used as a particulate anti-microbial/anti-dandruff agent in the anti-microbial compositions of the present invention.

The present invention may further comprise one or more keratolytic agents such as Salicylic Acid.

Additional anti-microbial actives of the present invention may include extracts of melaleuca (tea tree) and charcoal.

When present in the composition, the anti-dandruff active is included in an amount from about 0.01% to about 5%, preferably from about 0.1% to about 3%, and more preferably from about 0.3% to about 2%, by weight of the composition.

Particles

The compositions of the present invention optionally may comprise particles. Particles useful in the present invention can be inorganic, synthetic, or semi-synthetic. In the compositions of the present invention, it is preferable to incorporate no more than about 20%, more preferably no more than about 10% and even more preferably no more than 2%, by weight of the composition, of particles. In an embodiment of the present invention, the particles have an average mean particle size of less than about 300 μm.

Non-limiting examples of inorganic particles include colloidal silicas, fumed silicas, precipitated silicas, silica gels, magnesium silicate, glass particles, talcs, micas, sericites, and various natural and synthetic clays including bentonites, hectorites, and montmorillonites.

Examples of synthetic particles include silicone resins, poly(meth)acrylates, polyethylene, polyester, polypropylene, polystyrene, polyurethane, polyamide (e.g., Nylon®), epoxy resins, urea resins, acrylic powders, and the like.

Non-limiting examples of hybrid particles include sericite & crosslinked polystyrene hybrid powder, and mica and silica hybrid powder.

Opacifying Agents

The compositions of the present invention may also contain one or more opacifying agents. Opacifying agents are typically used in cleansing compositions to impart desired aesthetic benefits to the composition, such as color or pearlescence. In the compositions of the present invention, it is preferable to incorporate no more than about 20%, more preferably no more than about 10% and even more preferably no more than 2%, by weight of the composition, of opacifying agents.

Suitable opacifying agents include, for example, fumed silica, polymethylmethacrylate, micronized Teflon®, boron nitride, barium sulfate, acrylate polymers, aluminum silicate, aluminum starch octenylsuccinate, calcium silicate, cellulose, chalk, corn starch, diatomaceous earth, Fuller's earth, glyceryl starch, hydrated silica, magnesium carbonate, magnesium hydroxide, magnesium oxide, magnesium trisilicate, maltodextrin, microcrystalline cellulose, rice starch, silica, titanium dioxide, zinc laurate, zinc myristate, zinc neodecanoate, zinc rosinate, zinc stearate, polyethylene, alumina, attapulgite, calcium carbonate, calcium silicate, dextran, nylon, silica silylate, silk powder, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The opacifying agents may also comprise various organic and inorganic pigments. The organic pigments are generally various aromatic types including azo, indigoid, triphenylmethane, anthraquinone, and xanthine dyes. Inorganic pigments include iron oxides, ultramarine and chromium or chromium hydroxide colors, and mixtures thereof.

Suspending Agents

The compositions of the present invention may further comprise a suspending agent at concentrations effective for suspending water-insoluble material in dispersed form in the compositions or for modifying the viscosity of the composition. Such concentrations generally range from about 0.1% to about 10%, preferably from about 0.3% to about 5.0%, by weight of the composition, of suspending agent.

Suspending agents useful herein include anionic polymers and nonionic polymers. Useful herein are vinyl polymers such as cross linked acrylic acid polymers with the CTFA name Carbomer.

Paraffinic Hydrocarbons

The compositions of the present invention may contain one or more paraffinic hydrocarbons. Paraffinic hydrocarbons suitable for use in compositions of the present invention include those materials which are known for use in hair care or other personal care compositions, such as those having a vapor pressure at 1 atm of equal to or greater than about 21° C. (about 70° F.). Non-limiting examples include pentane and isopentane.

Propellants

The composition of the present invention also may contain one or more propellants. Propellants suitable for use in compositions of the present invention include those materials which are known for use in hair care or other personal care compositions, such as liquefied gas propellants and compressed gas propellants. Suitable propellants have a vapor pressure at 1 atm of less than about 21° C. (about 70° F.). Non-limiting examples of suitable propellants are alkanes, isoalkanes, haloalkanes, dimethyl ether, nitrogen, nitrous oxide, carbon dioxide, and mixtures thereof.

Other Optional Components

The compositions of the present invention may contain fragrance.

The compositions of the present invention may also contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts.

The compositions of the present invention may contain a mono- or divalent salt such as sodium chloride.

The compositions of the present invention may also contain chelating agents.

The compositions of present invention may further comprise materials useful for hair loss prevention and hair growth stimulants or agents.

Method of Making Personal Care Composition

The compositions of the present invention, in general, may be made by mixing the ingredients together at either room temperature or at elevated temperature, e.g., about 72° C. Heat only needs to be used if solid ingredients are in the composition. The ingredients are mixed at the batch processing temperature. Additional ingredients, including electrolytes, polymers, fragrance, and particles, may be added to the product at room temperature.

Method of Treating Hair or Skin

The personal care compositions of the present invention are used in a conventional manner for cleansing and conditioning hair or skin. Generally, a method of treating hair or skin of the present invention comprises applying the personal care composition of the present invention to the hair or skin. More specifically, an effective amount of the personal care composition is applied to the hair or skin, which has preferably been wetted with water, and then the personal care composition is rinsed off. Such effective amounts generally range from about 1 g to about 50 g, preferably from about 1 g to about 20 g. Application to the hair typically includes working the composition through the hair such that most or all of the hair is contacted with the composition.

This method for treating the hair or skin comprises the steps of: (a) applying an effective amount of the personal care composition to the hair or skin, and (b) rinsing the applied areas of hair or skin with water. These steps can be repeated as many times as desired to achieve the desired cleansing and conditioning benefit.

For use in methods of the present invention, the personal care composition may be in various forms, for example, shampoos, body washes, gels, lotions, creams, mousses, and sprays. For some of these forms, the personal care composition may be packaged in a pump-dispenser bottle or in an aerosol container. In other useful forms, the personal care composition may be dried to a film or a powder, or it may be applied to a substrate which is then used for application to the hair or skin.

NON-LIMITING EXAMPLES

The compositions illustrated in the following Examples illustrate specific embodiments of the compositions of the present invention, but are not intended to be limiting thereof. Other modifications can be undertaken by the skilled artisan without departing from the spirit and scope of this invention. These exemplified embodiments of the composition of the present invention provide enhanced deposition of conditioning agents to the hair and/or skin.

The compositions illustrated in the following Examples are prepared by conventional formulation and mixing methods, an example of which is described above. All exemplified amounts are listed as weight percents and exclude minor materials such as diluents, preservatives, color solutions, imagery ingredients, botanicals, and so forth, unless otherwise specified.

The following are representative of shampoo compositions of the present invention:

Non-Limiting Examples

Hompolymers

| EXAMPLE COMPOSITION | 1 | 2 | 3 | 4 | 5 | 6 | 7 | 8 | 9 | 10 |
|---|---|---|---|---|---|---|---|---|---|---|
| Anionic Surfactant [19] | | | 1 | 10 | 20 | 30 | 20 | 15 | 10 | 15 |
| Anionic Surfactant [18] | 1 | 10 | | | | | 10 | 5 | 5 | 20 |
| Sodium Lauroamphoacetate [14] | | | | | 2.00 | | | | | |
| Cocaminopropionic Acid [15] | | | | 1.00 | | | | | | |
| Cocamidopropyl Betaine [16] | | | | 1.00 | | | | | | |
| Cocamide MEA | 1.00 | 0.80 | 0.80 | 0.80 | 0.80 | 0.80 | 0.80 | 0.80 | 0.80 | 0.80 |
| Cetyl Alcohol | 0.35 | 0.90 | 0.60 | 0.60 | 0.60 | 0.60 | 0.60 | 0.60 | 0.60 | 0.60 |
| Lauryl Alcohol | 0.20 | | 0.35 | 0.35 | 0.35 | | | 0.35 | 0.35 | 0.35 |
| Dihydrogenated Tallowamidoethyl Hydroxyethylmonium Methosulfate [17] | | | 0.15 | 0.15 | 0.15 | 0.15 | 0.15 | 0.15 | 0.15 | 0.15 |
| 1-Propanaminium, N,N,N-trimethyl-3-[(2-methyl-1-oxo-2-propenyl)amino]-, chloride; | 0.40 [1] | 0.50 [1] | 0.40 [1] | 0.40 [1] | 0.40 [2] | | | | | |

-continued

| EXAMPLE COMPOSITION | 1 | 2 | 3 | 4 | 5 | 6 | 7 | 8 | 9 | 10 |
|---|---|---|---|---|---|---|---|---|---|---|
| (Poly(Methacrylamidopropyl trimethyl ammonium chloride)) [1, 2] | | | | | | | | | | |
| Methacryloamidopropyl-pentamethyl-1,3-propylene-2-ol-ammonium dichloride [3] | | | | | | 0.40 | | | | |
| 1-Propanaminium, N,N,N-trimethyl-3-[(1-oxo-2-propenyl)amino]-, chloride; (Poly(Acrylamidopropyl trimethyl ammonium chloride)) [4] | | | | | | | | 0.40 | | |
| [3-methacryloylamino)propyl] dimethylethylammonium ethylsulfate homopolymer [5] | | | | | | | | | 0.40 | |
| [(2-methacryloyloxy)ethyl]tri-methylammonium methylsulfate homopolymer [6] | | | | | | | | | | 0.40 |
| Ethylene Glycol Distearate | | 1.50 | 1.50 | 1.50 | 1.50 | 1.50 | 1.50 | 1.50 | 1.50 | 1.50 |
| Trihydroxystearin [7] | 0.25 | | | | | | | | | |
| Polyethylene Glycol (14000) [8] | | | 0.17 | 0.17 | 0.17 | 0.17 | 0.17 | 0.17 | 0.17 | 0.17 |
| Fragrance | 0.55 | 0.70 | 0.55 | 0.55 | 0.55 | 0.55 | 0.55 | 0.55 | 0.55 | 0.55 |
| Sodium Chloride | 0.30 | 1.30 | 0.80 | 0.80 | 0.80 | 0.80 | 0.80 | 0.80 | 0.80 | 0.80 |
| Ammonium Xylenesulfonate | 1.00 | | | | | | | | | |
| Citric Acid | 0.04 | 0.04 | 0.04 | 0.04 | 0.04 | 0.04 | 0.04 | 0.04 | 0.04 | 0.04 |
| Sodium Citrate | 0.40 | 0.40 | 0.40 | 0.40 | 0.40 | 0.40 | 0.40 | 0.40 | 0.40 | 0.40 |
| Sodium Benzoate | 0.25 | 0.25 | 0.25 | 0.25 | 0.25 | 0.25 | 0.25 | 0.25 | 0.25 | 0.25 |
| Ethylene Diamine Tetra Acetic Acid | 0.10 | 0.10 | 0.10 | 0.10 | 0.10 | 0.10 | 0.10 | 0.10 | 0.10 | 0.10 |
| Dimethicone [9, 10, 11] | | 2.35 [9] | 0.50 [9] | 2.00 [10] | 2.00 [11] | 0.80 [9] | 0.80 [9] | 0.50 [9] | 0.50 [9] | |
| Polydecene [12] | | 0.40 | | | | | | | | |
| Trimethylolpropane Tricaprylate/Tricaprate [13] | | 0.10 | | | | | | | | |
| Water and Minors (QS to 100%) | | | | | | | | | | |

[1] HMW MAPTAC (Rhodia) [charge density = 4.5 meq/g, molecular weight ~860,000]
[2] HHMW MAPTAC (Rhodia) [charge density = 4.5 meq/g, molecular weight ~1,500,000]
[3] Diquat (Rhodia) [charge density = 5.60 meq/g, molecular weight ~252,000]
[4] APTAC (Rhodia) [charge density = 4.88 meq/g, molecular weight ~1,916,000]
[5] Homopolymer of DMAPMA + DES (Rhodia) [charge density = 3.09 meq/g, molecular weight ~180,000]
[6] Homopolymer of METAMS (Rhodia) [charge density = 3.53 meq/g, molecular weight ~313,000]
[7] Thixcin R (Rheox)
[8] PEG 14M (Dow Chemical)
[9] Viscasil 330M (General Electric Silicones)
[10] Dow Corning ® 1664 Emulsion (Dow Corning)
[11] Dow Corning ® 2-1865 Microemulsion (Dow Corning)
[12] Puresyn 6, MCP-1812 (Mobil)
[13] Mobil P43 (Mobil)
[14] Miranol Ultra L32 (Rhodia)
[15] MACKAM 151C (McIntyre)
[16] Tegobetaine F-B (Goldschmidt)
[17] Varisoft 110 (Witco)
[18] A surfactant component according to the formula:

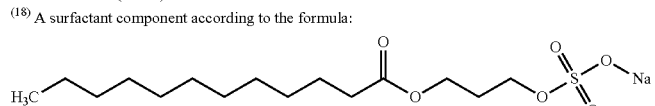

[19] A surfactant component according to the formula:

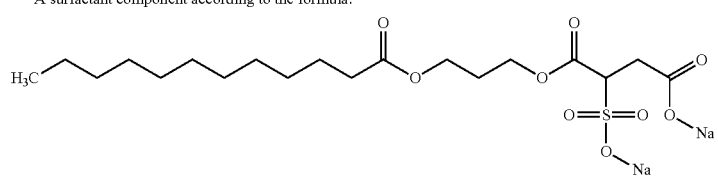

What is claimed is:

1. A surfactant represented by the formula:

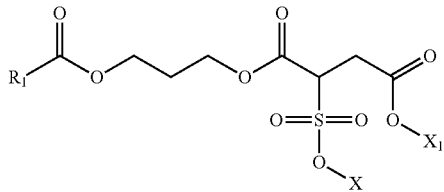

wherein $R_1$ is $C_8$-$C_{18}$ alkyl; and
X and $X_1$ are the same or different, and each is selected from $NH_4^+$, an alkali metal, or an H atom.

2. A surfactant according to claim 1, wherein said surfactant is naturally derived.

3. A surfactant according to claim 2, wherein said surfactant is derived from a monoester of vegetable oil fatty acids and 1,3-propanediol.

4. A surfactant according to claim 3, wherein said vegetable oil fatty acid is selected from the group consisting of coconut, palm, soybean, rapeseed, sunflower seed, peanut, cottonseed, palm kernel, and olive.

5. A surfactant according to claim 1, wherein said surfactant is a component of a personal care composition.

6. A surfactant according to claim 5, wherein said personal care composition comprises one or more ingredients selected from the group consisting of a conditioning agent, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculicides, pH adjusting agents, perfumes, preservatives, chelants, proteins, skin active agents, sunscreens, UV absorbers, and vitamins, wherein said ingredients are provided in a cosmetically acceptable medium.

7. A surfactant according to claim 5, wherein said personal care composition consists essentially of ingredients which are natural or naturally derived.

* * * * *